United States Patent
Murray et al.

(10) Patent No.: US 9,126,909 B2
(45) Date of Patent: Sep. 8, 2015

(54) HEAVY METAL REMEDIATION VIA SULFUR-MODIFIED BIO-OILS

(71) Applicant: The United States of America, as represented by the Secretary of Agriculture, Washington, DC (US)

(72) Inventors: Rex E. Murray, Peoria, IL (US); Grigor B. Bantchev, Peoria, IL (US); Kenneth M. Doll, Peoria, IL (US); Robert O. Dunn, Peoria, IL (US); Kim L. Ascherl, Peoria, IL (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 209 days.

(21) Appl. No.: 13/706,551

(22) Filed: Dec. 6, 2012

(65) Prior Publication Data
US 2014/0163248 A1 Jun. 12, 2014

(51) Int. Cl.
C07C 53/00 (2006.01)
C07C 323/50 (2006.01)
B01D 53/14 (2006.01)
B09C 1/08 (2006.01)
C02F 1/28 (2006.01)
C07C 321/02 (2006.01)
(Continued)

(52) U.S. Cl.
CPC .......... *C07C 323/50* (2013.01); *B01D 53/1493* (2013.01); *B09C 1/08* (2013.01); *C02F 1/286* (2013.01); *C02F 1/683* (2013.01); *C07C 321/02* (2013.01); *B01D 2252/205* (2013.01); *B01D 2257/60* (2013.01); *C02F 2101/20* (2013.01)

(58) Field of Classification Search
None
See application file for complete search history.

(56) References Cited

U.S. PATENT DOCUMENTS

| | | |
|---|---|---|
| 4,012,315 A | 3/1977 | Heilweil |
| 4,405,462 A | 9/1983 | Kamperman |
| 5,332,531 A | 7/1994 | Horwitz et al. |

(Continued)

FOREIGN PATENT DOCUMENTS

| | | | |
|---|---|---|---|
| JP | 46-16285 | * | 5/1971 |
| JP | S6168325 A | * | 4/1986 |
| WO | wo9965871 | | 12/1999 |

OTHER PUBLICATIONS

JP 46-16285, Dyeable Polypropylene fiber, 1971, Ohzeki et al., English abstract, 1 page.*

(Continued)

*Primary Examiner* — Yate K Cutliff
(74) *Attorney, Agent, or Firm* — John D. Fado; G. Byron Stover

(57) ABSTRACT

We have now discovered a novel process for the removal or extraction of metal species from a variety of solid, liquid or gas phase materials. Metal species may be removed by contacting the material suspected of containing one or more metals with a thiolated fatty acid or ester thereof for a period of time and under conditions effective for the sequestration of the metal species by the thiolated fatty acid or ester thereof. The thiolated fatty acid or ester thereof comprising sequestered metal species may then be separated and recovered from the treated material. Moreover, following the treatment of aqueous liquids or mixtures, or suspensions or dispersions of solids in aqueous liquids, the resultant thiolated fatty acid or ester thereof comprising the sequestered metal species is insoluble in water and forms a separate layer from the aqueous liquid phase, which layer may be readily removed.

11 Claims, 4 Drawing Sheets

(51) Int. Cl.
*C02F 1/68* (2006.01)
*C02F 101/20* (2006.01)

(56) References Cited

U.S. PATENT DOCUMENTS

| | | | | |
|---|---|---|---|---|
| 5,821,382 | A * | 10/1998 | Hino et al. | 560/146 |
| 6,689,907 | B1 * | 2/2004 | Labat | 562/512 |
| 7,557,236 | B2 | 7/2009 | Brown et al. | |
| 7,781,484 | B2 | 8/2010 | Byers et al. | |
| 7,989,655 | B2 | 8/2011 | Refvik et al. | |
| 2004/0158095 | A1 * | 8/2004 | Farone et al. | 560/153 |
| 2012/0225161 | A1 * | 9/2012 | Stark | 426/2 |

OTHER PUBLICATIONS

JPS6168325, Ioue Katsutoshi, Spearation of mercury by solvent extraction using carboxylic acid containing sulfur, 1986, English abstract (1 page).*

Mercier, L. et al., Heavy Metal Ion Adsorbents Formed by the Graftinf of a Thiol Functionality to Mesoporous Silica Molecular Sieves: Factors Affecting Hg(II) Uptake, Environ. Sci. Technol., 1998, pp. 2749-2754, vol. 32.

Murray, R.E. et al., Thioether-Functionalized Vegetable Oils: Metal-Absorbing Biobased Ligands, ACS Sustainable Chemistry and Engineering, 2013, pp. 562-565, vol. 1.

Yantasee, W. et al., Removal of Heavy Metals form Aqueous Systems with Thiol Functionalized Superparamagnetic Nanoparticles, Environ. Sci. Technol., 2007, pp. 5114-5119, vol. 41.

Bantchev, Grigor B., et al., "Free Radical Addition of Butanethiol to Vegetable Oil Double Bonds", J. Agric. Food Chem., 2009, 57, 1282-1290.

Bantchev, Grigor B., et al., "Temperature dependence of the oxidative stability of corn oil and polyalphaolefin in the presence of sulfides", Thermochimica Acta, 513, 2011, pp. 94-99.

Biresaw, Girma, et al, "Tribological Properties of Vegetable Oils Modified by Reaction with Butanethiol", Tribol. Lett, 2011, 43, pp. 17-32.

Hong, Kyung-Jin et al, "Evaluation of remediation process with plant-derived biosurfactant for recovery of heavy metals from contaminated soils", Chemosphere, 49, 2002, pp. 279-287.

Hoyle, Charles E., et al., Thiol-Enes: Chemistry of the Past with Promise for the Future, J. Polym. Sci., Part A: Polym. Chem: vol. 43, 2004, pp. 5301-5337.

Wang, Jianlong, et al., "Biosorbents for heavy metals removal and their future", Biotechnology Advances, 27, 2009, pp. 195-226.

Bromboerg, Lev, et al., "Reactive Silver and Cobalt Nanoparticles Modified with Fatty Acid Ligands Functionalized by Imidazole Derivatives", Chem. Mater., 2010, 22, pp. 5383-5391.

US Environmental Protection Agency, "Treatment Technologies for Mercury in Soil, Waste, and Water", Aug. 2007, Office of Superfund Remidation and Technology Innovation, Washington, DC 20460.

* cited by examiner

HEAVY METAL REMEDIATION VIA SULFUR-MODIFIED BIO-OILS

BACKGROUND OF THE INVENTION

1. Field of the Invention

The invention relates to methods for sequestering and removing metals from solid, liquid or gaseous materials using thiolated bio-oils.

2. Description of the Prior Art

Most vegetable oils typically have a triacylglycerol structure with a glycerol backbone connected to three long-chain ester linkages. The hydrocarbon chains of the structure make the molecule hydrophobic and immiscible with water or lower alcohols. The ester groups and internal double bonds give ample routes for modification (Gunstone. Fatty Acid and Lipid Chemistry. Blackie Academic and Professional. Glasgow, UK. 1994. 252). A wide variety of such vegetable oil derivatives have been reported (Biermann et al. 2000. Angew. Chem. Int. Ed. 39:2206-2224; Biermann et al. 2011. Angew. Chem. Int. Ed. Engl. 50:3854-3871; Hwang et al. 2003. J. Am. Oil. Chem. Soc. 80:811-815; Sharma et al. 2008. Bioresource Technol. 99:7333-7340; Ionescu et al. 2011. J. Serbian Chem. Soc. 76:591-606; Biswas et al. 2008. J. Agric. Food Chem. 56:5611-5616; Biswas et al. 2007. Green Chem. 9:85-89; Biswas et al. 2009. J. Agric. Food Chem. 57:8136-8141), having a variety of applications. These derivatives have included sulfurized vegetable oils obtained by the reaction between elemental sulfur and vegetable oils to improve the antiwear properties of lubricants (Erikson et al. U.S. Pat. No. 4,134,845; Kammann and Phillips. 1985. J. Am. Oil Chem. Soc. 62:917-923; Rossrucker and Fessenbecker. Sulfur carriers. In: Lubricant Additives: Chemistry and Applications. Rudnick. Ed. CRC Press. Boca Raton, Fla. 2003. pp. 259-292; McDonald. Zinc dithiophosphates. In: Lubricant Additives: Chemistry and Applications. Rudnick. Ed. CRC Press. Boca Raton, Fla. 2003. pp. 29-44; Walling and Helmreich. 1959. J. Am. Chem. Soc. 81:1144-1148). The addition of $H_2S$ or alkanethiols to fatty acids or their esters has also been widely described (Kircher. 1964. J. Am. Oil Chem. Soc. 41:351-354; Schwab et al. 1968. J. Am. Oil Chem. Soc. 45:461-464; Gadd et al. 1996. Eur. patent 0713867; Schwab and Gast. 1970. J. Am. Oil Chem. Soc. 47:371-373). The synthesis of hydroxyl-thioether derivatives of vegetable oil from epoxidized oils as lubricants was described by Sharma et al. (2006. J. Agric. Food Chem. 54:9866-9872) and Erhan et al. (U.S. Pat. No. 7,279,448). More recently, Bantchev et al. described the production of sulfide-modified vegetable oil lubricants using butanethiol in UV-initiated thiol-ene reactions with vegetable oils (2009. J. Agric. Food Chem. 57:1282-1290).

SUMMARY OF THE INVENTION

We have now discovered a novel process for the removal or extraction of metal species from a variety of solid, liquid or gas phase materials. Heavy metals and other metal species may be removed by contacting the material suspected of containing one or more metal species with a thiolated fatty acid or ester thereof, including thiolated glycerides, for a period of time and under conditions effective for the sequestration of the metal species by the thiolated fatty acid or its ester. The thiolated fatty acid or its ester comprising the sequestered metal species may then be separated and recovered from the treated material. Moreover, when treating aqueous liquids or mixtures, or suspensions or dispersions of solids in aqueous liquids, the thiolated fatty acid or its ester comprising the sequestered metal species is insoluble in water and forms a separate organic layer from the aqueous liquid layer which may be readily removed by simple techniques such as decantation or skimming.

In accordance with this discovery, it is an object of the invention to provide an improved bio-based method using modified fatty acids or their esters for removing metal species (including heavy metal species) from materials.

Another object of the invention to provide an improved bio-based method using modified fatty acid esters such as those of vegetable oils for removing metal species from materials.

A further object of this invention is to provide a method for removing metal species from water and other aqueous liquids wherein the metal species are partitioned into an organic liquid layer comprising a modified fatty acid or its ester.

Yet another object of this invention is to provide an improved method for removing metal contaminants from terrestrial and aquatic environments, and particularly from drinking water.

Other objects and advantages of the invention will become readily apparent from the ensuing description.

DETAILED DESCRIPTION OF THE INVENTION

Figure 1:
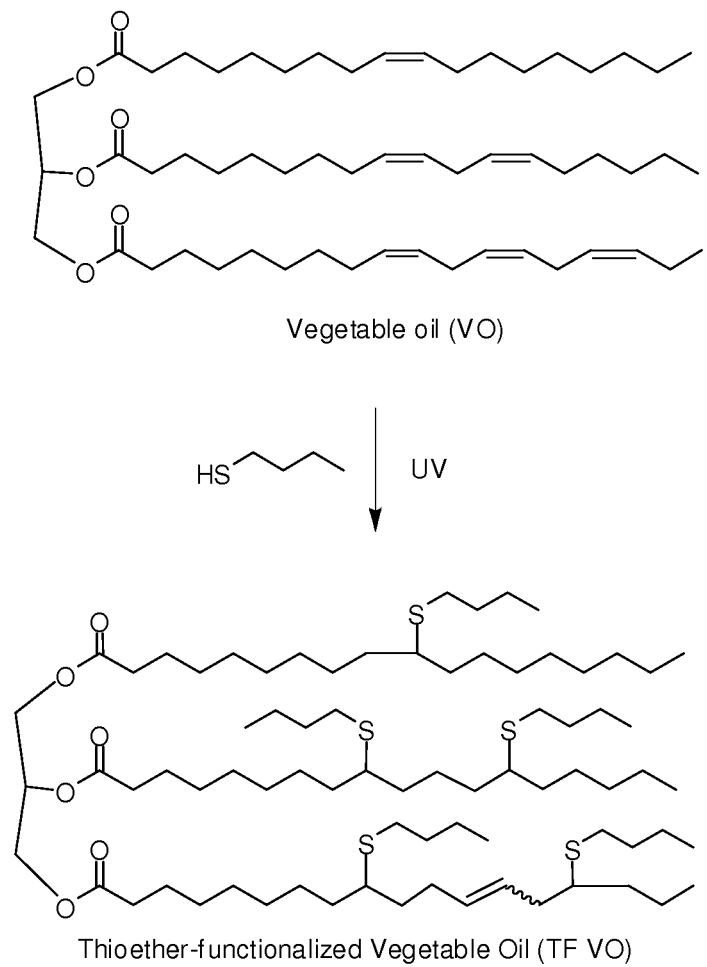
FIG. 1 shows a preferred method for the synthesis of thioether-functionalized vegetable oil (TF-VO) in accordance with Example 1.

Although thiolated glycerides and techniques for their production have been previously described, there is no demonstrated use of any of these compounds for the extraction of metal species from water or other materials. We have now discovered that thiolated fatty acids or their esters, including thiolated glycerides, effectively sequester a variety of metal species, including heavy metals, precious metals and other metals, and have developed a novel process for the removal or extraction of such metal species from a variety of materials. As used herein, the term "metal species" encompasses ionic metals (metal ions), covalent metals or covalent metal compounds, neutral metals (including zero oxidation state metal compounds and elemental metal forms), metal complexes (including mono- and poly-nuclear complexes), metal-containing compounds, metalloid compounds, metal colloids and metal nanoparticles. Moreover, owing to their insolubility in water, following the treatment of aqueous materials (including gaseous or solid materials dissolved or dispersed in an aqueous liquid), the resultant thiolated fatty acid or their esters having the metal species sequestered therein will form an organic layer or partition separate from the aqueous liquid. This organic layer containing the sequestered metal species may be readily removed from the aqueous layer using simple techniques such as by skimming or decantation, without the need for further treatments or processing. Using the process described herein, over 90% by weight of the metal species content, preferably 99% or more, can be removed from the material being treated.

As used herein, a "thiolated fatty acid or ester thereof" is defined as a fatty acid or ester thereof (including glycerol esters or alkyl esters) which contains one or more sulfhydryl (—SH or thiol), thioether (—SR) or polysulfide [(—S)$_n$—R, where n>1] functional groups. In the case of glycerol esters (i.e., a thiolated glyceride), the thiolated glyceride will include at least one fatty acid which contains one or more of the sulfhydryl (—SH or thiol), thioether (—SR) or polysulfide [(—S)$_n$—R, where n>1] functional groups. Without being limited thereto, R is selected from (1) aliphatic hydrocarbons which may be a straight or branched chain, substituted (including O, S, N or P-containing moieties, or intra- or inter-molecular linkages to the same or other fatty acids or their esters) or unsubstituted, and saturated or unsaturated, (2) carbon rings which may be substituted (as above) or unsubstituted, and saturated or unsaturated, and (3) and heterocyclic rings which may be substituted (as above) or unsubstituted, and saturated or unsaturated. In a preferred embodiment, R is selected from (1) aliphatic C1 to C22 hydrocarbons which may be a straight or branched chain, substituted or unsubstituted, and saturated or unsaturated, (2) C5 to C18 carbon rings which may be substituted or unsubstituted, and saturated or unsaturated, and (3) C4 to C6 heterocyclic rings which may be substituted or unsubstituted, and saturated or unsaturated.

The process may be used for the removal of metal species contaminants from a variety of liquid, gaseous or solid materials, including those from aquatic and terrestrial systems. Moreover, as described herein, liquid materials may include solutions, emulsions, dispersions or biological fluids. Without being limited thereto, examples of such applications include the removal of toxic metals from contaminated drinking water and other fresh water systems (such as lakes, ponds, estuaries, rivers and streams), from effluent or waste discharge streams of agricultural, municipal (sewage), industrial or mining sites, from flue gases discharged from commercial or industrial sites, and from contaminated soil from agricultural, residential, industrial and mining sites. Alternatively, the process can be used to remove and recover potentially valuable metals from other materials. Examples of such applications include but are not limited to the recovery of metals from recycled materials and mining applications. Further still, it is envisioned that the process may be used for the differential removal or separation of two or more metals from each other. As illustrated in the examples, we have discovered that not only do different thiolated glycerides exhibit different levels of efficacy in their ability to sequester a particular metal species, but specific thiolated glycerides differ in the ability to sequester different metal species. By selection of the appropriate thiolated fatty acid or ester, materials containing two or more different metals may be treated to selectively remove more of one of the metals than the other.

The thiolated fatty acids and their esters are effective for the sequestration of many different metal species from any of the above-mentioned materials. Without wishing to being bound by theory, the mechanism of sequestration of the metals may be by binding, coordination, adsorption, absorption or a combination thereof. Without being limited thereto, the process is effective for sequestering and removing metal species which include B [including B(0) and B(III)], Be [including Be (0) and Be(II)], Ba [including Ba(0) and Ba(II)], Mn [including Mn(0), Mn(II), Mn(III), Mn(IV), Mn(VI) and Mn(VII)], Sb [including Sb(0), Sb(III), Sb(IV) and Sb(V)], Se [including Se(0), Se(II), Se(IV) and Se(VI)], Sr [including Sr(0), Sr(II)], Tl [including Tl(0), Tl(I) and Tl(III)], V [including V(0), V(II), V(III), V(IV) and V(V)], Cu [including Cu(0), Cu(I) and Cu(II)], Pb [including Pb(0), Pb(II) and Pb(IV)], Zn [including Zn(0) and Zn(II)], Cd [including Cd(0) and Cd(II)], Ni [including Ni(0) and Ni(II)], Cr [including Cr(0), Cr(III), Cr(IV) and Cr(VI)], Hg [including Hg(0), Hg(I) and Hg(II)], Fe [including Fe(0), Fe(II) and Fe(III)], Al [including Al(0) and Al(III)], Co [including Co(0) and Co(II)], Bi [including Bi(0), Bi(III) and Bi(V)], Sn [including Sn(0), Sn(II) and Sn(IV)], Ca [including Ca(0) and Ca(II)], Mg [including Mg(0) and Mg(II)], Ag [including Ag(0) and Ag(I)], As [including As(0), As(II), As(III) and As(V)], Mo [including Mo(0), Mo(II), Mo(III), Mo(IV), Mo(V) and Mo(VI)], Au [including Au(0), Au(I) and Au(III)], Rh [including Rh(0), Rh(I) and Rh(III)], Ir [including Ir(0), Ir(I), Ir(II), Ir(III), Ir(IV) and Ir(VI)], Os [including Os(0), Os(II), Os(III), Os(IV), Os(VI) and Os(VIII)], Re [including Re(0), Re(IV), Re(VI) and Re(VII)], Pd [including Pd(0), Pd(II), Pd(III) and Pd(IV)], Pt [including Pt(0), Pt(II) and Pt(IV)], Ru [including Ru(0), Ru(I), Ru(III), Ru(IV), Ru(V), Ru(VI) and Ru(VIII)], and combinations thereof. However, the process is particularly preferred for the removal of Cu(II), Al(III), Pb(II), Cd(II), Bi(III), and Bi(V), and most preferably Hg(II), Ag(I).

In accordance with applicants' process, the material suspected of containing or being contaminated with the metals is contacted with the thiolated fatty acid or ester thereof (which is in a liquid phase) for a period of time and under conditions effective for the metal species in the material to be sequestered by the thiolated fatty acid or its ester. The specific contact time will vary with the material being treated and particularly its phase (solid, liquid or gas), the type of contactor used as discussed below, and the metal species concentration in the treated material and the desired final concentration therein (i.e., complete vs. partial removal), and may be readily determined empirically by the skilled user. The contact time will typically be sufficient to remove between 5 to 100% (by weight), preferably between 50 to 99%, and most preferably between 70 to 99%, of the targeted metal species present in the material. After this contact, the resultant thiolated fatty acid or their esters having the metals sequestered therein may be separated from the treated material. The remaining treated material, having its metal content significantly reduced or eliminated, may be subsequently recovered. The process may be conducted as a batch, semi-batch or continuous system. In an optional embodiment, the recovered treated materials, and particularly those processed in batch or semi-batch systems, may be contacted one or more times with fresh thiolated fatty acid or ester to further decrease the metal species concentration therein to the desired level.

Treatment of liquid materials, and particularly aqueous liquids, may be conducted in a variety of conventional liquid/liquid contactor devices. A number of liquid/liquid contact devices have been described for other liquid/liquid extractions and are suitable for use herein, and include mixed tanks (or mixer-settlers), spray columns, fixed beds (including packed beds or grid or mesh beds), moving beds or fluid beds, plate (or tray) columns, mechanically assisted gravity devices and centrifugal extractors, with mixed tanks and plate columns being preferred, and mixed tanks being particularly preferred. When using mixed-tanks, the contact of the material with the thiolated fatty acid or its ester can be enhanced, and thus the rate and amount of metal sequestration increased, by increased agitation, and is preferred. Without being limited thereto, examples of liquid/liquid contactors which are suitable for use herein are described by Henley and Saeder (Equilibrium-Stage Separation Operations in Chemical Engineering, John Wiley and Sons, New York, 1981, see pp. 47-85, the contents of which are incorporated by reference herein). Upon completion of the contacting, the resultant thiolated fatty acid or ester thereof comprising the sequestered metal species is separated from the treated material. In the preferred embodiment using mixed-tanks for treating aqueous liquids, upon completion of the contacting, agitation is ceased, and the resultant thiolated fatty acid or ester thereof comprising the sequestered metal species is allowed to form a separate (partitioned) organic layer from the aqueous liquid phase. This separate organic layer may be separated or removed from the treated aqueous layer and optionally recovered, for example by conventional techniques such as decantation, skimming, draining of the aqueous layer, etc.

Gaseous materials including flue gases may be contacted with the thiolated fatty acid or its ester in a variety of conventional vapor/liquid contact devices, many of which are similar to the above-mentioned liquid/liquid contactors. Suitable vapor/liquid contactors include scrubbers, mechanical-draft evaporative-cooling devices, bubblers, spray columns, fixed beds (including packed beds or grid or mesh beds), moving beds or fluid beds, and plate (or tray) columns. Without being limited thereto, examples of vapor/liquid contactors which are suitable for use herein are also described by Henley and Saeder (ibid, see pp. 47-76). The thiolated fatty acid or its ester may also be absorbed on a solid substance (ideally porous) for contact with the gaseous material. After contacting, the resultant thiolated fatty acid or ester thereof comprising the sequestered metal species is separated from the gas. The treated gaseous material stripped of metal species may be released to the atmosphere or recovered and optionally further treated. By way of example, this embodiment of the process is preferably used for the removal of volatile covalent metal compounds such as dimethyl mercury or elemental mercury, Hg(0), from gaseous materials.

Contact of solid materials with the thiolated fatty acid or its ester may also be conducted in a variety of conventional solid/liquid contact devices, including packed beds or moving beds (with gravity or anti-gravity flow of the thiolated fatty acid or its ester through the bed of solid material to be treated) or mixed tanks, with mixed tanks being preferred. As with liquid/liquid contact, increased agitation is preferred. After contacting, the resultant thiolated fatty acid or ester thereof comprising the sequestered metal species is separated from the solid. Separation may be effected, for example, by settling, centrifugation or filtration. The treated solid material stripped of metal species may be recovered and optionally further treated. With any solid material, the material may be optionally physically ground prior to the contacting in order to increase the surface area of the material and the exposure of metals therein to the thiolated fatty acids or esters thereof. Moreover, it is also envisioned that soils may be optionally chemically digested to release any metals therein for contact with the thiolated fatty acids or their esters. A number of techniques for soil digestion have been previously described for measurement of soil nutrients and other chemicals, and are suitable for use herein. Without being limited thereto, the soil digestion with 1 M ammonium acetate or Mehlich 3 reagent (glacial acetic acid with ammonium nitrate, ammonium fluoride, nitric acid and EDTA) as described by Warncke and Brown (Potassium and Other Basic Cations. In: Recommended Chemical Soil Test Procedures for the North Central Region. North Central Regional research Publication No. 221. Missouri Agricultural Experiment Station SB 1001. Rev. January 1998. pp. 31-33) or Mehlich (1984. Comm. Soil Sci. Plant Anal. 15:1409-1416) or using the original technique described by Mehlich (1953, Determination of P, Ca, Mg, K, Na and NH4 by North Carolina Soil Testing Laboratories. Raleigh, University of North Carolina) is preferred. In alternative embodiment, it is also envisioned that the solid material to be treated may be dissolved or dispersed in a liquid material or solvent, such as water or other aqueous solvent or carrier, and contacted with the thiolated fatty acid or its ester using the liquid/liquid contactors as described above.

After the thiolated fatty acid or ester thereof comprising the sequestered metal species have been separated from the treated material, it may be disposed of in an environmentally appropriate manner. However, in a preferred embodiment, the thiolated fatty acid or ester thereof comprising the sequestered metal species is recovered and treated to remove the sequestered metals and optionally regenerate the thiolated fatty acid or ester. In one preferred embodiment, ionic or other higher than zero oxidation state covalent forms of the metals are reduced, producing the metal in a solid phase. A variety of techniques are known in the art for metal ion reduction and are suitable for use herein, including electrolytic, chemical or photochemical reduction. Without being limited thereto, suitable reduction techniques are described, for example, by Wu et al. (2011. Recovery of metallic copper by integrated chemical reduction and high gradient magnetic separation. Environ. Technol. 32:817-824) and Parinayok et al. (2011. Interaction of Au(III) and Pt(IV) complex ions with Fe(II) ions as a scavenging and a reducing agent: A basic study on the recovery of Au and Pt by a chemical method. Journal of Colloid and Interface Science. 364:272-275), the contents of each of which are incorporated by reference herein). The resultant metal solids may be recovered by filtration, centrifugation, magnetic separation, settling or decantation, and the resultant thiolated fatty acid or ester retained and optionally recycled. In an alternative embodiment, an additional reagent may be added to the thiolated fatty acid or ester thereof comprising the sequestered metal species which would cause the formation of an insoluble metal complex and precipitation. This solid precipitate could be removed as above. Examples of precipitating agents include but are not limited to halogen ions. For example, a solution containing $Cl^-$ ions could be added to a $Ag^+$ saturated thiolated fatty acid or ester thereof. The resultant solid AgCl may be recovered, as well as the regenerated thiolated fatty acid or ester thereof. In accordance with yet another alternative embodiment, it is envisioned that a solution containing another ion binding compound, such as EDTA, having a greater binding affinity (or binding constant) for the metal species than the thiolated fatty acid or its ester may be contacted with the thiolated fatty acid or ester thereof comprising the sequestered metal species which would result in the transfer of the metal species into that solution. In another alternative embodiment, metal species can be separated from the thiolated fatty acid or ester thereof by oxidation, such as with hydrogen peroxide, bleach, ozone or other oxidizing agent which could oxidize the soft sulfur to a hard sulfoxide or hard sulfone ligand, and thereby release the soft metal to an aqueous phase, and/or oxidize the metal to a higher oxidation state.

Figure 2:
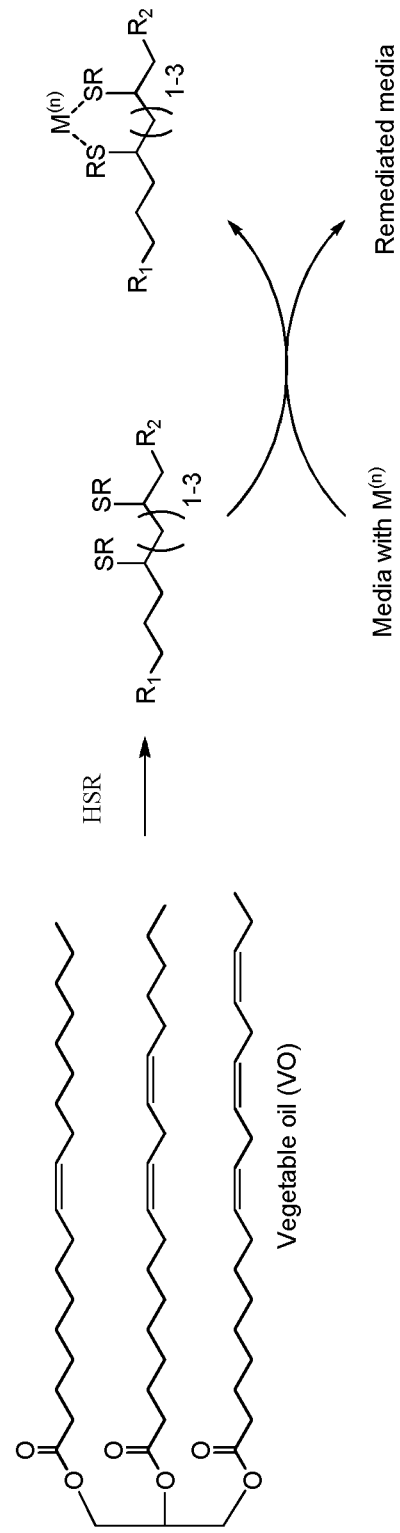
FIG. 2 shows a summary of the reaction scheme for the synthesis of TF-VO and a potential mechanism for its subsequent sequestration of metal species from media as described in Example 1.

As noted above, a number of techniques for producing the thiolated fatty acids or esters thereof have been previously described and are suitable for use herein. Moreover, these compounds may be produced by reaction of free fatty acids or their esters (including alkyl esters and glycerides). In accordance with a preferred embodiment, the thiolated fatty acids or esters thereof are produced by the photolytic free-radical addition of aliphatic-thiols to unsaturated vegetable oils as described by Bantchev et al. (2009, ibid, the contents of which are incorporated by reference herein). It is envisioned that this process may also be used with free unsaturated fatty acids or other esters thereof, including fatty acid alkyl esters. Briefly, an unsaturated fatty acid or ester thereof (including glycerides having one or more sites of unsaturation) is reacted with an thiol (such as butanethiol) at a molar ratio of approximately 6 mol of alkanethiol per mol of double bonds in the fatty acid, ester or glyceride, with application of UV irradiation ($\lambda \leq 325$ nm). An optional photoinitiator such as 2,2-dimethoxy-2-phenylacetophenone, may be added. The reaction produces a thioether modified fatty acid or ester with the thioether moieties introduced at the sites of unsaturation such as shown in FIG. 2. The thioether modified fatty acid or ester can be recovered by methanol washing or distillation. In an optional embodiment, for reactions using a glyceride starting material such as an unsaturated vegetable oil, the reaction product (a thioether modified vegetable oil) may be transesterified into a thioether-modified fatty acid alkyl ester by reaction with an alkyl alcohol (such as methanol or ethanol) in KOH with heat at 100° C., also as described by Bantchev et al. (2009, ibid). In another optional embodiment, the fatty acid chains of the glyceride may be covalently bonded to other chains in the same or different glycerides (or transesterified to alkyd type resins as well), using thermal methods such as described by Erhan and Bagby (1994. J. Amer. Oil Chem. Soc. 71:1223), or through the addition of strong acids as described by Liu and Erhan (2010. J. Polym. Enviro. 18:243), the contents of each of which are incorporated by reference herein.

As noted above, the thiolated fatty acids or esters thereof may also be produced by a number of other techniques which have been previously described. Suitable techniques which may be used include, but are not limited to, those described by Erhan et al. (U.S. Pat. No. 7,279,448) for the production of poly(hydroxylthioether) vegetable oil derivatives; Refyik (U.S. Pat. No. 7,989,655) for the production of thiol esters, hydroxyl thiol esters and cross-linked thiol esters; Erikson et al. (U.S. Pat. No. 4,134,845), Kammann and Phillips (1985. J. Am. Oil Chem. Soc. 62:917-923), Rossrucker and Fessenbecker (Sulfur carriers. In: Lubricant Additives: Chemistry and Applications. Rudnick. Ed. CRC Press. Boca Raton, Fla. 2003. pp. 259-292), McDonald (Zinc dithiophosphates. In: Lubricant Additives: Chemistry and Applications. Rudnick. Ed. CRC Press. Boca Raton, Fla. 2003. pp. 29-44) and Walling and Helmreich (1959. J. Am. Chem. Soc. 81:1144-1148), all describing the production of sulfurized vegetable oils by the reaction between elemental sulfur and vegetable oils; and Kircher (1964. J. Am. Oil Chem. Soc. 41:351-354), Schwab et al. (1968. J. Am. Oil Chem. Soc. 45:461-464), Gadd et al. (1996. Eur. patent 0713867), Schwab and Gast (1970. J. Am. Oil Chem. Soc. 47:371-373) all describing the addition of $H_2S$ or alkanethiols to fatty acids or their esters. The contents of each of the above-mentioned patents and publications are incorporated by reference herein.

The thiolated fatty acids or esters thereof are preferably produced from a variety of unsaturated fatty acids (olefins), including vegetable oils, animal fats, algal oils or marine oils (including fish and krill oils), or alkyl esters of vegetable oils, animal fats, algal oils or marine oils. The starting unsaturated fatty acid is not critical, and any $\Delta^2$ to $\Delta^{29}$ unsaturated fatty acid (i.e. having a double bond between $\Delta^2$ to $\Delta^{29}$ inclusive) containing from 4 to 30 carbon atoms or longer may be used. Thus, starting fatty acids include fatty acids of the formula $R_4'$-COOR' wherein $R_4'$ is a straight or branched chain olefin, and R' is H, branched or straight chain alkyl or alkenyl groups, aromatic containing groups, or glycerides (including mono-, di- or triglycerides). Preferred starting fatty acids include, but are not limited to free and esterified, $\Delta^3$ to $\Delta^{17}$ unsaturated or polyunsaturated fatty acids containing from 4 to 22 carbon atoms, more particularly free and esterified $\Delta^3$ to $\Delta^{17}$ unsaturated or polyunsaturated fatty acids containing from 8 to 22 carbon atoms, and most particularly free and esterified $\Delta^9$ to $\Delta^{15}$ unsaturated or polyunsaturated fatty acids containing from 8 to 22 carbon atoms. Examples of particularly preferred unsaturated fatty acids which may be used herein include free and esterified palmitoleic acid (16:1, $\Delta^9$), oleic acid (18:1, $\Delta^9$), linoleic acid (18:2, $\Delta^{9,1}$), erucic acid (22:1, $\Delta^{13}$), and linolenic acid (18:3, $\Delta^{9,12,15}$), 5-eicosenoic acid (20:1, $\Delta^5$), 5-docosenoioc acid (22:1, $\Delta^5$), 5,13-docosadienoic acid (22:2, $\Delta^{5,13}$), petroselinic acid (16:1, $\Delta^6$), and trans isomers of any of the above such as elaidic acid (18:1, $\Delta^9$). It is also understood that the starting fatty acids (and the resultant thiolated fatty acids or esters) may include fatty acids wherein $R_4'$ is substituted and/or includes a cyclic carbon moiety such as the cyclopropenyl moiety or the like from *Sterculis foetida* (Java Olive oil), and may also include dimer acids.

Unsaturated fatty acids are naturally occurring in a variety of plant oils or animal fats and may be conveniently obtained for use therefrom. Without being limited thereto, oils which may be used as sources include soybean, cottonseed, corn, olive, peanut, palm, sesame, sunflower, canola, castor, safflower, linseed, grapeseed, oiticia, tung, rice, crambe, vernonia (ironweed), tobacco seed, algae, animal fat, high erucic rape, *Sterculis foetida* (Java olive oil), and high oleic canola oils, with soybean oil, canola oil and corn oil being particularly preferred.

As starting materials to prepare the epoxides, the unsaturated fatty acids may be provided in substantially pure form or, in the alternative, they may be provided as a mixture or in impure form. Moreover, although the unsaturated fatty acids may be free acids, the thiolated fatty acids or esters thereof may be prepared from fatty acids which are esterified with aliphatic alcohols such as methanol, ethanol, isopropanol, or branched chain alcohols such as 2-ethyl hexanol or Guerbet alcohols, or with glycerol as mono-, di- or triglycerides. However, because fatty acids occur predominantly as triglycerides in triglyceride oils, the above-mentioned naturally occurring oils are preferably used directly in the reaction, thereby foregoing the need for any preliminary fatty acid synthesis and isolation of the oil.

In a preferred embodiment wherein the fatty acids are present as triglycerides, the oils principally contemplated herein include what are normally referred to as the triglyceride drying oils. The vegetable triglyceride drying oils include plant oils and plant source-like synthetic and semi-synthetic triglycerides that can be transformed into hard, resinous materials [see Encyclopedia of Polymer Science and Technology, H. F. Monk et al., eds., John Wiley & Sons, (1966), pp. 216-234]. The expression "drying oils" is generic to both true drying oils, which dry (harden) at normal atmospheric conditions, and semidrying oils, which must be baked at elevated temperatures in order to harden. Unless otherwise indicated, "drying oil" will be used herein in its broadest sense to refer to both types of drying oil. The unsaturated fatty acids (e.g., linoleic or linolenic) residues of a drying or semi-drying oil comprise double bonds that are readily available for entering into an oxidative reaction, or other reactions involved in the drying process. These oils may also include oleic fatty acid residues. Common sources of drying oils include cottonseed oil, castor oil, canola oil, linseed oil, oiticica oil, safflower oil, soybean oil, sunflower oil, corn oil, and tung oil.

The generic chemical structure of triglyceride oils for use in the invention is represented by the formula, below:

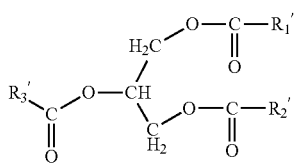

wherein $R_1'$, $R_2'$, $R_2'$ and $R_3'$ are independently selected from C3 to C29 aliphatic fatty acid residues, that may be completely saturated or have sites of unsaturation and/or hydroxylation, provided that $R_2'$, $R_2'$ and $R_3'$ collectively have at least 1 but preferably more sites of unsaturation. As noted above, the aliphatic fatty acid residues $R_2'$, $R_2'$ and $R_3'$ may also be substituted and/or include a cyclic carbon moiety such as the cyclopropenyl moiety or the like from *Sterculis foetida* (Java Olive oil), and may also include dimer acids. In most of the common triglyceride oils listed above, the triglyceride esters are composed of C18 and C16 fatty acids, and accordingly $R_1'$, $R_2'$, and $R_3'$ are C17 or C15.

The practitioner skilled in the art will of course recognize that for thiolated fatty acids or esters thereof requiring a high degree of purity or uniformity, the oils may first be hydrolyzed to obtain free fatty acids for use as starting materials in the reaction to produce the thiolated fatty acids. Hydrolysis of the oils to the fatty acids may be achieved using conventional splitting techniques or alkali splitting of fats. Suitable alkali splitting techniques include, for example, treatment with sodium methoxide, or sodium or potassium hydroxide [see "A.O.C.S. Tentative Method Ca 6b-53", in: Official and Tentative Methods of the American Oil Chemist's Society, third edition, AOCS, Chicago, Ill., (1973)]. Other conventional techniques including splitting with steam under pressure are also effective.

Using the preferred fatty acid and fatty acid ester starting materials described above, the thiolated fatty acid or ester thereof will comprise a C4 to C30 fatty acid comprising one or more of the —SH or —SR moieties, wherein R is defined above. Thiolated glycerides will be of the formula:

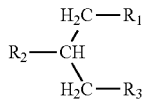

wherein $R_1$, $R_2$, and $R_3$ are independently selected from (a) —OH, (b) a C4 to C30 aliphatic fatty acid moiety, and (c) a C4 to C30 aliphatic fatty acid moiety comprising one or more —SH, —SR or $(-S)_n$—R moieties linked thereto, with the proviso that at least one of the $R_1$, $R_2$, and $R_3$ comprise a C4 to C30 aliphatic fatty acid moiety comprising one or more of the —SH, —SR or —(S)$_n$—R moieties (wherein R is described above). In accordance with this formula, the C4 to C30 aliphatic fatty acid moieties of (b) and (c) may be independently represented by the formula $R_4$—C(O)O—, wherein $R_4$ is a straight or branched chain hydrocarbon which may be saturated or unsaturated, and substituted or non-substituted. $R_4$ may also include a cyclic carbon moiety such as the cyclopropenyl moiety or the like from *Sterculis foetida* (Java Olive oil), or a cyclic sulfur-containing moiety, such as a tetrahydrothiophene and/or thiane ring and may also include polymerized glycerides as well as dimer acids (intra- or inter-molecular), wherein the term "dimer acid" encompasses two fatty acids joined by a sulfide bond —S—, $(-S-)_n$—, or —SR$_6$S— where $R_6$ is an organic bi-radical.

The following example is intended only to further illustrate the invention and is not intended to limit the scope of the invention which is defined by the claims.

Example 1

Materials

Corn and canola oils used in this study were obtained from a local retailer. Thioether functionalized (TF) corn and canola oils were produced by reacting them with excess butanethiol using a UV light according to Bantchev et al. (2009. ibid). Purification was done by distillation instead of the chromatography also employed by Bantchev et al. (2009. ibid). Elemental analyses show sulfur content of 9.7% for TF-corn oil and 10% for TF-canola oil. Silver nitrate was obtained from Sigma Aldrich (St. Louis, Mo.). Analytical standards were obtained from Spex Certiprep (Metuchen, N.J.). The water used for the samples was purified by reverse osmosis.

Silver Extraction Procedures

Extractions were run by two different methods. In the experiments for capacity determination, samples of 1 mL of ~600 ppm silver nitrate solution were added to samples of TF-VO ranging in mass from 0.004 g to 0.104 g. A micro stir-bar was added and the foil wrapped reaction vials were placed in a Pierce Reacti-therm (Rockford, Ill.) 9-place stirring block and allowed to stir for 11 days to ensure equilibration between the Ag$^+$ solution and the TF-VO. Aliquots of the aqueous layer were taken and analyzed on a Perkin-Elmer Optima 7000DV inductively coupled plasma spectroscope (Waltham, Mass.) at 328.068 nm.

In the rate of extraction experiments, 3 mL of stock solution was added to 0.3 g of oil. These samples were vortexed for 1 min and then foil wrapped. Aliquots were taken at appropriate time periods with a pipette and analyzed as above.

Results and Discussion:

Synthesized Products

Through the reaction process outlined in FIG. 2, it is evident that the composition of acyl chains of the starting material determines the oil's potential for conversion to the ligand modified system. The saturated fatty chains have no active reaction site while the mono-unsaturated (oleic), di-unsaturated (linoleic), and tri-unsaturated (linolenic) have one, two, and three sites. The characterization in Bantchev et al. (2009. ibid) demonstrated that, under the reaction conditions employed here, there is no preference of thiol molecule incorporation into a specific double bond type. Therefore, the fatty chain composition of the starting oil will be projected onto the product thioether functionalized vegetable oil (TF-VO). The differences in the three unsaturated components: 28%, 56%, and 1% in corn oil; 63%, 19%, and 9% in canola oil, show the possibility of producing TF-VOs with similar sulfur content, yet different structure. For example, TF-canola oil has ~65% of its chains incorporating one thioether group but only ~20% incorporating two. TF-corn oil has a different distribution, 39% with one and 37% with two thioether groups.

Comparison of the Extraction Performance of the Vegetable Oil and TF-VO

Ag$^+$ Extractions with TF-VO: Capacity Experiments

The capacities for Ag$^+$ absorption by corn oil, TF-corn oil, and TF-canola oil were evaluated by determining how much silver could be removed from a stock solution at extraction times over 72 h. The data, shown in Table 1, displays several interesting trends. First, corn oil with no added ligands showed essentially no ability to remove the Ag$^+$ from the aqueous solution. Second, TF-corn oil is able to decrease the silver concentration in the water below the detection limit. Finally, TF-canola oil was also effective but much less effective than the TF-corn oil. For example, when 0.07-0.08 g of the TF-VO was used, all of the $Ag^+$ detectable was extracted in the TF-corn oil system, but 34% was left by TF-canola oil. Even more telling is that the TF-canola oil system with even more oil, 0.1 g, was no more effective than the system with lower amounts of TF-corn oil.

TABLE 1

The concentration of $Ag^+$ detected in aqueous solution after extraction with the specified amount of TF-VO or ordinary corn oil, using the capacity method.

| corn oil | | TF-corn oil | | TF-canola oil | |
|---|---|---|---|---|---|
| oil (g) | [Ag] (ppm) | Oil (g) | [Ag] (ppm) | Oil (g) | [Ag] (ppm) |
| 0 | 600 | 0 | 600 | 0 | 600 |
| 0.0074 | 604 | 0.0023 | 549 | 0.0037 | 510 |
| 0.0285 | 627 | 0.0338 | 134 | 0.0317 | 311 |
| 0.0476 | 608 | 0.0480 | 58 | 0.0484 | 251 |
| 0.0761 | 615 | 0.0723 | ND | 0.0802 | 208 |
| 0.1057 | 604 | 0.1006 | ND | 0.1040 | 235 |

Figure 3:
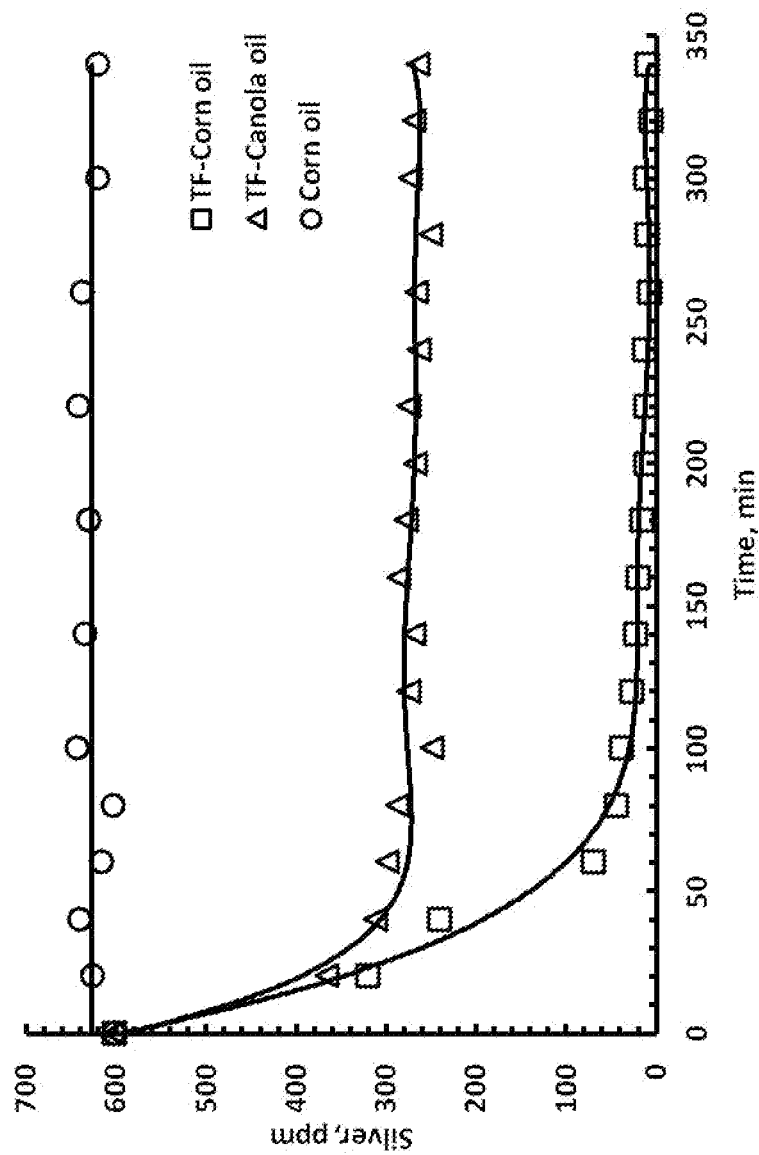
FIG. 3 shows observed $Ag^+$ concentration of aliquots of a solution stirred with the TF-VO and ordinary corn oil using the rate of extraction method as described in Example 1.

ND = below detection limit of 0.5 ppm $Ag^+$ extractions with TF-VO: Rate of extraction experiments As in the capacity experiments, three oil systems were tested in the extraction of $Ag^+$: ordinary corn oil, TF-corn oil, and TF-canola oil. The data in FIG. 3 show that both of the TF-VOs can remove the $Ag^+$ in a relatively short time. In the TF-corn oil, more than 90% of the $Ag^+$ was removed from the water within 80 min. The TF-canola oil also reached its maximum absorption, just over 50% of the silver, in roughly the same time frame. As before, essentially no capacity for metal absorption was noticed for the corn oil, which also serves as a control experiment for the system in general. In other words, no experimental artifact caused the observed decrease in the concentration of $Ag^+$.

Absorption Differences

The data show that the modification of the double bonds into thioether groups gives the capability for extraction of metal species from the aqueous solution as both of the TF-VO samples removed appreciable $Ag^+$, with efficiencies between 69 and >99%. The TF-corn oil exhibited metal-removal capacities comparable to more elaborate ligand systems, such as the thiacrown (Baumann et al. 2000. Reactive and Functional Polymers. 44:111-120; Baumann et al. 1998. Chem. Commun. 16:1637-1638), which contains poly-dentate thioether ring structures.

The significantly higher efficacy of TF-corn oil relative to TF-canola oil was achieved even though the sulfur content of the oils, by weight, was essentially the same. Also, the $Ag^+$ capacity of TF-corn oil remains high even as the silver concentration in the aqueous phase approaches single digit values. The system can be analyzed with the equilibrium absorption constant model shown in Scheme 2.

Scheme 2. The equation of the equilibrium absorption constant for TF-VO with $Ag^+$.

From the data presented in Table 1, taking the point where 0.048 g of oil was used, the ratio of $Ag^+_{(captured\ in\ the\ oil)}/Ag^+_{(still\ observed\ in\ solution)}$ is a metric that compares the system efficiency. The TF-corn oil has a ratio of 542/58 whereas TF-canola oil has a ratio of 349/251, i.e. 9.3 vs. 1.4, showing TF-corn oil to be ~6.6 times more effective under these conditions. At this stage, there is no sufficient evidence to decide unambiguously on the best-performing structure(s) and how to maximize their content in the product. However, a couple of broad generalizations are implied. First, TF-canola oil had more mono-thioether chains, yet lower absorption, indicating that this is a less effective binding motif. TF-corn oil had more di-thioether chains, so there is the possibility of a strong binding chelate effect. TF-canola oil actually has more tri-thioether chains, but does not seem to gain additional adsorption beyond di-thioether chains from them. Finally, the TF-corn oil also has many more chains which contain both one thioether and an unreacted double bond. It is possible that a synergistic bi-dentate hemi-labile type complex in which both a double bond and sulfur coordinate to the metal is stronger than a mono-dentate sulfur coordination. Further effects, such as the number of sulfur atoms on neighboring chains, are also possible. In summary, chemical modification of vegetable oils represents an inexpensive and convenient way to utilize an agriculturally-based approach to solve a serious problem relating to heavy metal pollution and water purification, and can also be viewed as a method for precious metal recovery.

Example 2

Thiolated corn oil and canola oil were prepared as described in example 1 and contacted with aqueous solutions of different metal ions as shown in Table 2. TF-corn 1 was the same oil from Example 1, while TF-corn 2 was the same sample but was further purified by heating under vacuum. Samples of oil were mixed with 1.00 mL of heavy metal solution purchased from inorganic ventures (lot #C2-TM01065). Samples were vortexed for 1 min and then allowed to settle in darkness for 1 week. After removal of the thiolated oil from the aqueous solutions, the amount of the metal ion remaining in the solution was determined and the % of ion removed calculated. Metal analysis was conducted in the same manner and with the same instrumentation as Example 1 (using the characteristic wavelength for every metal ion). The results are shown in Table 2.

TABLE 2

| | Amount of ion removed from aqueous solution (%) | | | | | | | | | | | | | | | | | | | | |
|---|---|---|---|---|---|---|---|---|---|---|---|---|---|---|---|---|---|---|---|---|---|
| Oil tested | Ag | Al | As | B | Ba | Be | Cd | Co | Cr | Cu | Fe | Mn | Mo | Ni | Pb | Sb | Se | Sr | Tl | V | Zn |
| TF-canola | 98 | 3 | 10 | 5 | 6 | 6 | 6 | 5 | 5 | — | 6 | 5 | 5 | 5 | 5 | 8 | 15 | 5 | 7 | 6 | 5 |
| TF-corn | 99 | 8 | 13 | 0 | 8 | 9 | 8 | 7 | 8 | 8 | 8 | 7 | 7 | 8 | 9 | 9 | 9 | 8 | 13 | 7 | 8 |
| TF-corn 2 | 74 | 8 | 10 | 7 | 8 | 9 | 7 | 7 | 7 | 8 | 8 | 7 | 7 | 6 | 8 | 7 | 15 | 8 | 6 | 7 | 9 |

Example 3

Figure 4:
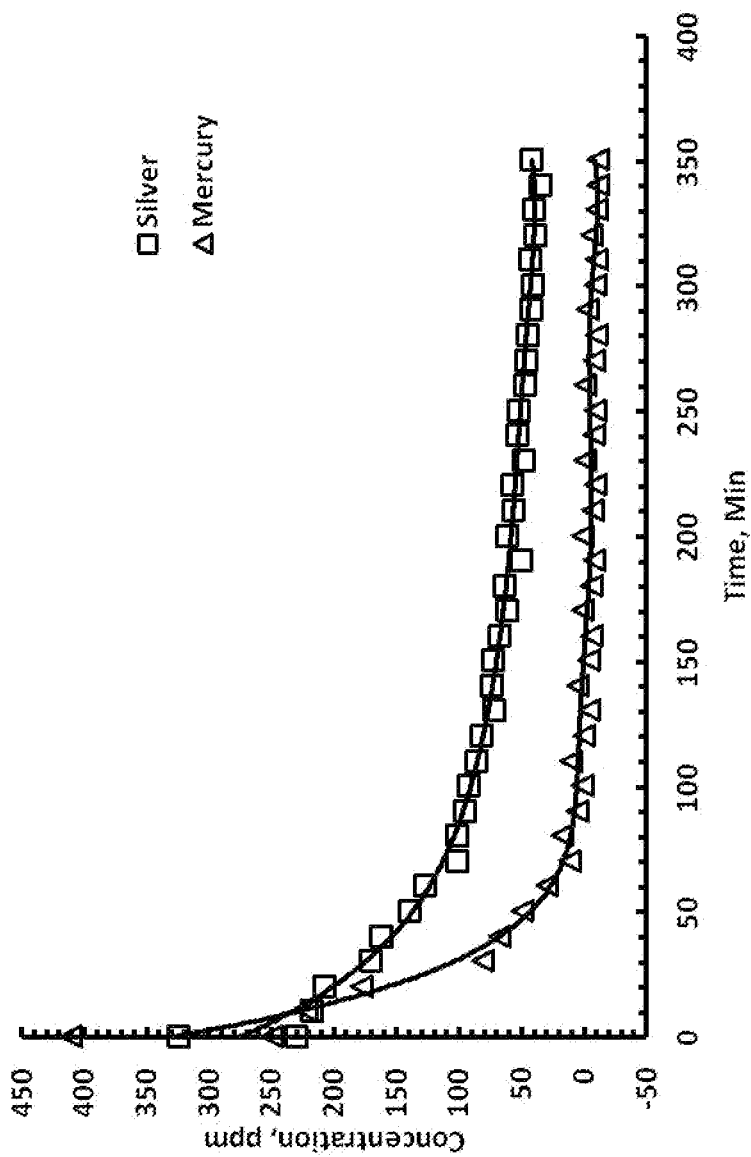
FIG. 4 shows observed $Ag^+$ and $Hg^{2+}$ concentrations of aliquots of a solution stirred with the TF-VO using the rate of extraction method as described in Example 3.

A 2 mL aliquot of silver stock solution and 2 mL of mercury stock solution were combined in a scintillation vial. TF-oil (0.2013 g), as made in example 1, was added to the vial. The mixture was vortexed for 1 min. A 100 µL portion was taken and subsequently diluted volumetrically to 10 mL. A sample was taken every 10 minutes for approximately 3 hours. The samples were then tested on the ICP at 328.068 nm for silver and 253.652 nm for mercury. The results are shown in FIG. 4. The results demonstrate the preferential sequestration of Hg by TF-oil relative to Ag, and thus the separation of Hg from Ag. Specifically, Hg is removed much faster and more completely than Ag when treated with TF-oil.

It is understood that the foregoing detailed description is given merely by way of illustration and that modifications and variations may be made therein without departing from the spirit and scope of the invention.

We claim:

1. A thiolated fatty acid or ester thereof comprising one or more sequestered metal species bound to sulfur in said thiolated fatty acid or ester.

2. The thiolated fatty acid or ester thereof of claim 1 wherein said metal species are selected from the group consisting of B, Be, Ba, Mn, Sb, Se, Sr, Tl, V, Cu, Pb, Zn, Cd, Ni, Cr, Hg, Fe, Al, Co, Bi, Sn, Ca, Mg, Ag, As, Mo, Au, Rh, Ir, Os, Re, Pd, Pt, Ru and combinations thereof.

3. The thiolated fatty acid or ester thereof of claim 2 wherein said metal species are selected from the group consisting of Cu, Al, Pb, Cd, Bi, Bi, Hg, Ag and combinations thereof.

4. The thiolated fatty acid or ester thereof of claim 3 wherein said metal species are selected from the group consisting of Hg, Ag and combinations thereof.

5. The thiolated fatty acid or ester thereof of claim 1 wherein said thiolated fatty acid or ester thereof comprise one or more —SH, —SR or $(-S)_n$—R moieties wherein n is an integer greater than 1 and R is selected from the group consisting of (1) an aliphatic hydrocarbon which may be a straight or branched chain, substituted or unsubstituted, and saturated or unsaturated, (2) a carbon ring which may be substituted or unsubstituted, and saturated or unsaturated, and (3) and a heterocyclic ring which may be substituted or unsubstituted, and saturated or unsaturated.

6. The thiolated fatty acid or ester thereof of claim 5 wherein said thiolated fatty acid or ester thereof comprises a C4 to C30 fatty acid comprising one or more of said —SH, —SR or $(-S)_n$—R moieties.

7. The thiolated fatty acid or ester thereof of claim 1 wherein said thiolated fatty acid or ester thereof comprises a thiolated glyceride of the formula:

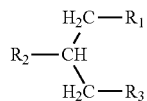

wherein $R_1$, $R_2$, and $R_3$ are independently selected from (a) —OH, (b) a C4 to C30 aliphatic fatty acid moiety, and (c) a C4 to C30 aliphatic fatty acid moiety comprising one or more —SH, —SR or $(-S)_n$—R moieties linked thereto wherein n is an integer greater than 1 and R is selected from the group consisting of (1) an aliphatic hydrocarbon which may be a straight or branched chain, substituted or unsubstituted, and saturated or unsaturated, (2) a carbon ring which may be substituted or unsubstituted, and saturated or unsaturated, and (3) and a heterocyclic ring which may be substituted or unsubstituted, and saturated or unsaturated; with the proviso that at least one of said $R_1$, $R_2$, and $R_3$ comprise said C4 to C30 aliphatic fatty acid moiety comprising one or more of said —SH, —SR or $(-S)_n$—R moieties.

8. The thiolated fatty acid or ester thereof of claim 7 wherein said aliphatic fatty acid moiety of (b) and (c) are of the formula $R_4$—C(O)O—, wherein $R_4$ is a C3 to C29 straight or branched chain hydrocarbon which may be saturated or unsaturated, and substituted or unsubstituted.

9. A thiolated fatty acid or ester thereof comprising one or more sequestered metal species, wherein said metal species are selected from the group consisting of Hg, Ag and combinations thereof.

10. A thiolated fatty acid or ester thereof comprising one or more sequestered metal species, wherein said thiolated fatty acid or ester thereof comprises a thiolated glyceride of the formula:

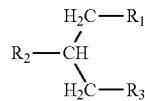

wherein $R_1$, $R_2$, and $R_3$ are independently selected from (a) —OH, (b) a C4 to C30 aliphatic fatty acid moiety, and (c) a C4 to C30 aliphatic fatty acid moiety comprising one or more —SH, —SR or $(-S)_n$—R moieties linked thereto wherein n is an integer greater than 1 and R is selected from the group consisting of (1) an aliphatic hydrocarbon which may be a straight or branched chain, substituted or unsubstituted, and saturated or unsaturated, (2) a carbon ring which may be substituted or unsubstituted, and saturated or unsaturated, and (3) and a heterocyclic ring which may be substituted or unsubstituted, and saturated or unsaturated; with the proviso that at least one of said $R_1$, $R_2$, and $R_3$ comprise said C4 to C30 aliphatic fatty acid moiety comprising one or more of said —SH, —SR or $(-S)_n$—R moieties.

11. A thiolated fatty acid or ester thereof comprising one or more sequestered metal species, wherein said thiolated fatty acid or ester thereof comprises a thiolated glyceride of the formula:

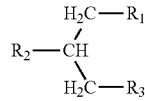

wherein $R_1$, $R_2$, and $R_3$ are independently selected from (a) —OH, (b) a C4 to C30 aliphatic fatty acid moiety, and (c) a C4 to C30 aliphatic fatty acid moiety comprising one or more —SH, —SR or $(-S)_n$—R moieties linked thereto wherein n is an integer greater than 1 and R is selected from the group consisting of (1) an aliphatic hydrocarbon which may be a straight or branched chain, substituted or unsubstituted, and saturated or unsaturated, (2) a carbon ring which may be substituted or unsubstituted, and saturated or unsaturated, and (3) and a heterocyclic ring which may be substituted or unsubstituted, and saturated or unsaturated; with the proviso that at least one of said $R_1$, $R_2$, and $R_3$ comprise said C4 to C30 aliphatic fatty acid moiety comprising one or more of said —SH, —SR or (—S)$_n$—R moieties; wherein said aliphatic fatty acid moiety of (b) and (c) are of the formula R$_4$—C(O)O—, wherein R$_4$ is a C3 to C29 straight or branched chain hydrocarbon which may be saturated or unsaturated, and substituted or unsubstituted.

* * * * *